United States Patent [19]

Abel et al.

[11] 4,265,760
[45] May 5, 1981

[54] DEVICE FOR DILUTION AND DELIVERY OF IN VIVO CHEMICALS

[75] Inventors: Kenneth Abel; Robert T. Buck, both of Raleigh, N.C.

[73] Assignee: Becton Dickinson & Company, Paramus, N.J.

[21] Appl. No.: 15,480

[22] Filed: Feb. 26, 1979

[51] Int. Cl.³ .......................................... B01D 27/02
[52] U.S. Cl. ............................. 210/282; 128/214 C; 210/446; 210/927; 210/321.2
[58] Field of Search ..................... 128/213 A, 214 C; 210/DIG. 23, DIG. 24, 317, 321 A, 448, 489, 495, 499, 282

[56] References Cited

U.S. PATENT DOCUMENTS

| | | | |
|---|---|---|---|
| 2,473,153 | 6/1949 | Lager | 210/448 |
| 2,644,586 | 7/1953 | Cutter | 210/448 X |
| 3,223,619 | 12/1965 | Calmon et al. | 210/24 R |
| 3,390,677 | 7/1968 | Razimbaud | 210/448 |
| 3,545,438 | 12/1970 | De Vries | 128/213 |
| 3,707,967 | 1/1973 | Kitrilakis et al. | 128/213 |
| 3,817,389 | 6/1974 | Weichselbaum | 210/448 |
| 3,882,026 | 5/1975 | McPhee | 128/214 C |
| 3,976,073 | 8/1976 | Quick et al. | 128/214 C |
| 4,035,304 | 7/1977 | Watenabe | 210/317 |
| 4,061,807 | 12/1977 | Shalev et al. | 210/502 |
| 4,081,372 | 3/1978 | Atkin et al. | 210/321 A |
| 4,127,131 | 11/1978 | Vallancoylt | 210/448 |
| 4,131,544 | 12/1978 | Elahi | 210/502 |
| 4,162,220 | 7/1979 | Servas | 128/214 |

OTHER PUBLICATIONS

Early Clinical Trials with Sorbents–Yatzidis et al., pp. 215-217, Kidney International, vol. 10 (1976).

Primary Examiner—Theodore A. Granger
Attorney, Agent, or Firm—Louis E. Marn; Elliot M. Olstein

[57] ABSTRACT

A collapsible disposable container for dilution and delivery of chemicals for in vivo use which includes a combination adsorbent and absolute filter for effecting sterilization and removal of endotoxins and organic contaminants from a diluent introduced into the container prior to in vivo use thereof. Such combination may be in the container inlet, container outlet or in the main storage portion thereof. Unsterilized diluent can be employed for diluting chemicals in the container.

11 Claims, 6 Drawing Figures

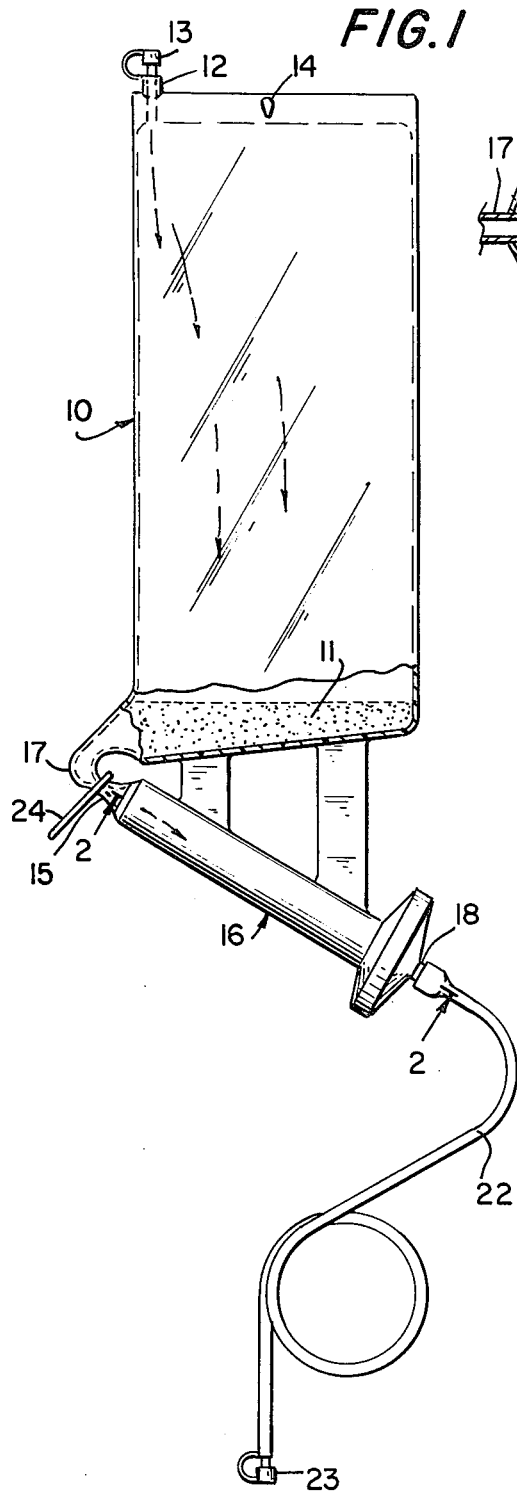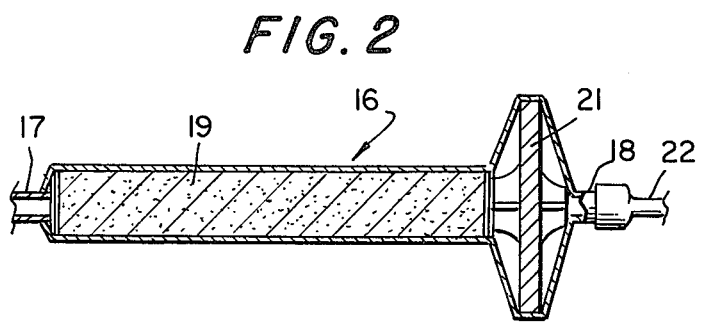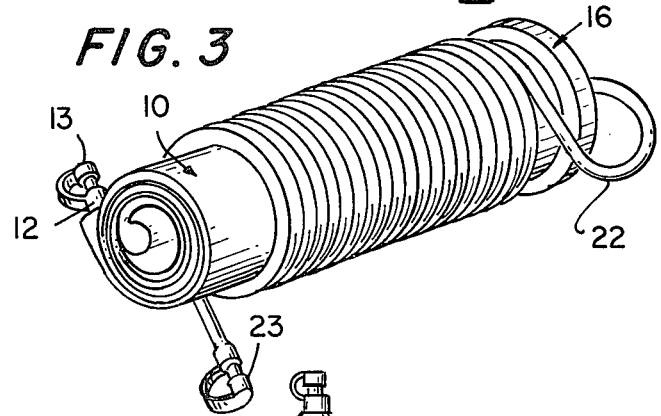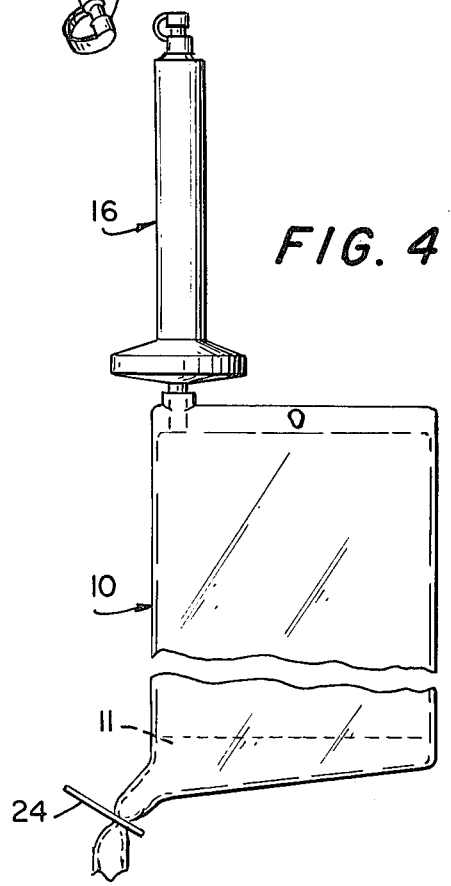

DEVICE FOR DILUTION AND DELIVERY OF IN VIVO CHEMICALS

This invention relates to a device for the storage and delivery of chemicals, requiring dilution, for in vivo use thereof.

Aqueous diluted chemicals for in vivo use are generally presterilized endotoxin free solutions which require shipment and storage of large volumes. As a result of the water bulk, there are storage problems, and in addition, there are shelf-life considerations resulting from such pre-dilution.

In accordance with the present invention, there is provided a device for dilution and delivery of chemicals for in vivo use, with the diluent being sterilized prior to delivery from the container for in vivo use thereof. In this manner, an unsterilized diluent can be employed for dilution of chemicals in the device.

More particularly, in accordance with the present invention, there is provided a collapsible, disposable container for delivering diluted chemicals for in vivo use which includes an inlet means and an outlet means, with the container further including a combination adsorbent and absolute filter for effecting sterilization and removal of endotoxins and organic contaminants from the diluent prior to in vivo use thereof. The combination of adsorbent and absolute filter may be in the container inlet means, container outlet means or in the main storage portion of the container. In this manner, when the chemicals are to be employed in a diluted form for in vivo use, unsterilized diluent, of suitable quality, which depending upon location may be domestic tap water, deionized water or distilled water, is introduced into the container to effect dilution of the chemicals, with such diluent contacting the adsorbent and absolute filter prior to in vivo use thereof to thereby effect sterilization and removal of endotoxins and organic contaminants. In this manner dry or liquid concentrated chemicals can be diluted in the container with dilution water prior to use of the chemicals to thereby eliminate the storage and shipping problems resulting from the use of prediluted chemicals.

The absolute filter employed in the device of the present invention is a filter having a pore size of no greater than $0.45\mu$ with the pore size generally being in the range of from 0.10 to $0.25\mu$. The absolute filter functions to remove solid contaminants from the diluted chemicals, with such contaminants generally being bacteria, spores, and particulates, such as sand, and other debris.

The adsorbent employed in the device of the present invention is generally activated charcoal, zeolites, etc., with activated charcoal alone or in combination with zeolites being preferred. The selection of a suitable adsorbent is deemed to be within the scope of those skilled in the art from the teachings herein. The adsorbent functions to separate from the diluted chemicals low molecular weight organics, chloramines, chlorine, pyrogens, virus, and odor producing materials.

The device of the present invention is particularly suitable for administration of a peritoneal lavage solution; however, it is also suitable for other in vivo uses. Thus, for example, the device may be employed for medical applications including, but not limited to: acute peritoneal dialysis; chronic peritoneal dialysis and parenteral solutions, including intravenous drug administration; plasma extender administration; Ringer's Lactate and similar I.V. solutions; intravenous feeding; and other parenteral solutions requiring on-site mixture.

The invention will be further described with respect to embodiments thereof illustrated in the accompanying drawing; however, the scope of the invention is not to be limited thereby:

FIG. 1 is a simplified elevation view of an embodiment of the device of the present invention;

FIG. 2 is a cross-sectional view of the cartridge portion of the device of FIG. 1;

FIG. 3 is a simplified isometric view of the packaged configuration of of the device of FIG. 1;

FIG. 4 is a simplified elevation view of another embodiment of the device of the present invention;

Figure 5:
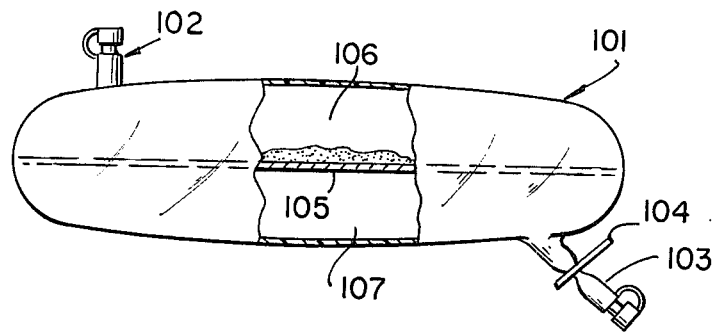
FIG. 5 is a simplified view of still another embodiment of the present invention.

Referring now to the drawings, there is shown in FIG. 1 a device in accordance with the invention which is comprised of a disposable, collapsible container, in the form of a flexible bag 10, constructed of a suitable material, such as a flexible polymer; e.g., plasticized polyvinyl chloride, polyurethanes, etc. The bag 10 contains dry chemicals or a concentrate thereof, schematically indicated as 11, with such chemicals being suitable for subsequent in vivo use in a diluted form. The bag 10 is of a size sufficient to hold the chemicals 11 in a water diluted state for in vivio use thereof.

The bag 10 includes a suitable inlet means for introducing unsterilized water, in the form of a filling port 12, which includes a removable cap 13. The top of the bag 10 is further provided with a suitable hanging tab 14 for hanging the bag, as known in the art, for delivery of diluted chemicals.

The bag 10 includes an outlet means for delivery of water diluted chemicals comprised of an outlet port 15 and a cartridge 16 which houses an adsorbent-absolute filter combination for effecting sterilization of the diluted chemicals and removal of endotoxins and organic contaminants. As shown in FIG. 2, the cartridge 16 includes an inlet port 17 and an outlet port 18, with the inlet portion of the cartridge including a suitable adsorbent, such as activated charcoal, schematically indicated as 19, and the outlet portion an absolute filter, designated as 21. It is to be understood that the order of the adsorbent and absolute filter could be changed, with the filter being placed in the inlet portion and the adsorbent in the outlet portion; however, such an arrangement is less preferred in that solid adsorbent particles may be included in the diluted chemicals. Suitable delivery tubing 22 is connected to the outlet port 18 of cartridge 16 with the outlet of the delivery tubing 22 including a suitable removable cap, designated as 23. A suitable removable pinch clamp 24 is employed to close communication between the outlet port 15 of the bag 10 and the inlet port 17 of the cartridge 16.

A packaged configuration of the device of the present invention is shown in FIG. 3. As shown in FIG. 3, the bag 10 is wound around cartridge 16, with the delivery tubing 22 then being wound around bag 10, whereby the device, containing the undiluted chemicals has a small bulk.

In accordance with the preferred embodiment, the device of the present invention is packaged with the dry or concentrated chemicals therein, with the device being shipped in the packaged configuration shown in FIG. 3. When the chemicals are to be diluted for in vivo use thereof, the bag may be suitably hung through the hanger tab 14, as known in the art, and the chemicals diluted to the appropriate concentration by the addition of water through inlet port 13. The connecting tube 22 is then connected to a suitable means for delivering the chemicals for in vivo use. Thus, for example, in the case of peritoneal lavage, the tube 22 may be connected to a peritoneal catheter. After the appropriate connection, the pinch clamp 24 is removed, and the appropriately diluted chemicals flow through the cartridge 16 containing the adsorbent 19 and filter 21 to effect sterilization and removal of endotoxin and organic contaminants for in vivo delivery through the connecting tube 22.

It is to be understood that modifications of the hereinabove described embodiment are possible in light of the above teachings. Thus, for example, it is possible to ship the device without the dry chemicals or concentrated chemicals being present therein. In such a case, the chemicals would be added to the bag prior to the addition of water.

As a further modification, as shown in FIG. 4 of the drawings, the cartridge containing the adsorbent and absolute filter can be placed in the inlet means of the container whereby the aqueous diluent flows through the adsorbent and absolute filter prior to being introduced into the main portion of the container for dilution of the chemicals for subsequent in vivo use.

A further modification of the device of the present invention is shown in FIG. 5. As shown in FIG. 5, the device is comprised of a disposable, collapsible container, in the form of a flexible bag 101 which includes an inlet means 102 for introduction of unsterilized diluent, and an outlet means 103. The outlet means 103 includes a pinch clamp 104 to close the outlet 103.

The interior of the container 101 is divided into an inlet compartment 106 and an outlet compartment 107 by an absolute filter 105. The inlet compartment includes the chemicals in dry or concentrated form which are to be diluted for in vivo use, as well as the solid adsorbent.

In accordance with this embodiment, the water diluent is introduced through the inlet means to effect dilution of the chemicals in inlet compartment 106, with the diluent contacting the adsorbent and flowing through the absolute filter 105 into the outlet compartment 107 for delivering the chemicals in diluted form for in vivo use through outlet means 103. Thus, as with the embodiments of FIGS. 1 through 3 and FIG. 4, chemicals to be employed for in vivo use in diluted form are diluted in the container by the use of unsterilized water, of suitable quality, with sterilization being effected prior to in vivo use thereof. As a result, it is possible to provide the chemicals for in vivo use in undiluted form, with dilution being effected immediately prior to use thereof.

Figure 6:
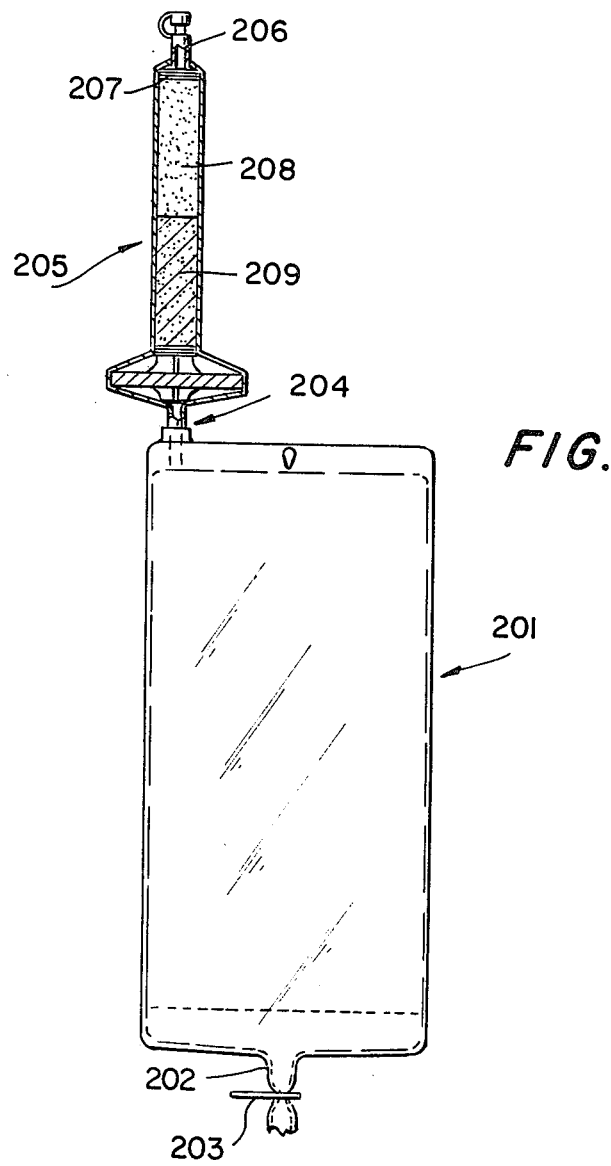
FIG. 6 is a simplified view of yet a further embodiment of the device of the present invention.

In another modification, as shown in FIG. 6, ther is provided a collapsible container 201, including a suitable outlet means 202, closed by a pinch clamp 203 and an inlet means 204, with the inlet means 204 including a cartridge 205 which houses an adsorbent-absolute filter combination for effecting sterilization and removal of endotoxins and organic contaminants, as well as storing chemicals for in vivo use. As shown, the cartridge 205 includes an inlet 206, a prefilter 207, chemicals to be diluted for in vivo use 208, an adsorbent 209 and an absolute filter 211. In accordance with this embodiment, water introduced into the cartridge 205 through the inlet 206 flows through prefilter 207, and mixes with the chemicals 208 to effect dissolution thereof. The diluted chemicals then flow through adsorbent 209 and absolute filter 211 into the container 201 for subsequent delivery for in vivo use through outlet 202. As with the previously described embodiments, the chemicals can be stored in undiluted form, with dilution of the chemicals being effected prior to use thereof with unsterilized water, with the diluent being sterilized for in vivo use by passage through the adsorbent and absolute filter.

The above modifications and others should be apparent to those skilled in the art from the teachings herein.

The present invention is considered to be particularly advantageous in that it permits shipping and storage of chemicals to be employed in vivo without dilution thereof, with the subsequent dilution of the chemicals being easily effected by the use of unsterilized water at the site of use. The device provides for sterilization and removal of contaminants prior to in vivo use thereof. Moreover such a result is achieved with a completely disposable unit, which can be provided at low cost.

Numerous modifications and variations of the present invention are possible in light of the above teachings and, therefore, within the scope of the appended claims, the invention may be practised otherwise than as particularly described.

We claim:

1. A device for dilution and delivery of diluted chemicals for in vivo use, comprising:

a disposable, collapsible flexible container for dilution and delivery of diluted chemicals for in vivo use, said container having an inlet means at one end and an outlet means at a second opposite end; a cartridge having an inlet end and an outlet end, an adsorbent for adsorbing contaminants in said cartridge adjacent said inlet end, an absolute filter having a pore size of no greater than $0.45\mu$ in said cartridge adjacent said outlet end, said outlet end of said cartridge being attached to said inlet means of said container, whereby unsterilized diluent can be introduced into the container by passing through the inlet end of the cartridge, the adsorbent, the absolute filter and the inlet means of the container for effecting sterilization and removal of endotoxins and organic contaminants from the diluent and diluted chemicals delivered from the container through the outlet means thereof for in vivo use.

2. The device of claim 1 wherein the container further includes the chemicals to be diluted whereby the chemicals are stored in the container in undiluted form.

3. The device of claim 2 wherein said chemicals are chemicals which in a diluted state are suited for peritoneal dialysis.

4. The device of claim 3 wherein the adsorbent is comprised of activated charcoal.

5. The device of claim 4 wherein the absolute filter has a pore size from 0.1 to $0.25\mu$.

6. A device for dilution and delivery of diluted chemicals for in vivo use, comprising:

a disposable, collapsible flexible container for dilution and delivery of diluted chemicals for in vivo use, said container including an inlet means at one end and an outlet means at a second opposite end; a cartridge having an inlet end and an outlet end, an adsorbent for adsorbing contaminants with said cartridge adjacent said inlet end and an absolute filter having a pore size of no greater than $0.45\mu$ within said cartridge adjacent said outlet end, said inlet end of said cartridge being attached to said outlet means of said container, whereby unsterilized diluent can be introduced into the container through the inlet means for dilution of chemicals therein and the diluted chemicals pass from the outlet means of the container through the adsorbent and absolute filter in said cartridge for effecting sterilization and removal of endotoxins and organic contaminants prior to in vivo use by delivery from the outlet end of the cartridge.

7. The device of claim 6 wherein the container further includes the chemicals to be diluted whereby the chemicals are stored in the container in undiluted form.

8. The device of claim 7 wherein said chemicals are chemicals which in a diluted state are suitable for peritoneal dialysis.

9. The device of claim 8 wherein the adsorbent is comprised of activated charcoal.

10. The device of claim 9 wherein the absolute filter has a pore size from 0.1 to $0.25\mu$.

11. The device of claim 6 and further comprising flexible tubing means attached to the outlet end of said filter.

* * * * *